United States Patent [19]
Kjell

[11] Patent Number: 5,808,047
[45] Date of Patent: Sep. 15, 1998

[54] PROCESS FOR THE PREPARATION OF 2,2'-ANHYDRO- AND 2'-KETO-1-(3',5'-DI-O-PROTECTED-β-D-ARABINOFURANOSYL) NUCLEOSIDES

[75] Inventor: Douglas P. Kjell, West Lafayette, Ind.

[73] Assignee: Eli Lilly and Company, Indianapolis, Ind.

[21] Appl. No.: 732,947

[22] Filed: Oct. 17, 1996

Related U.S. Application Data

[63] Continuation of Ser. No. 409,568, Mar. 24, 1995, abandoned.
[51] Int. Cl.$^6$ .................................................. C07H 19/09
[52] U.S. Cl. ........................ 536/27.11; 56/27.1; 56/28.5; 56/28.51; 56/28.52; 56/124
[58] Field of Search ............................... 536/27.11, 27.1, 536/28.5, 28.51, 28.52, 28.53, 28.54, 28.55, 124

[56] References Cited

U.S. PATENT DOCUMENTS

| | | | |
|---|---|---|---|
| 4,526,988 | 7/1985 | Hertel | 549/313 |
| 4,652,554 | 3/1987 | Chwang | 514/49 |
| 4,808,614 | 2/1989 | Hertel | 514/45 |
| 4,965,374 | 10/1990 | Chou et al. | 549/313 |
| 5,047,520 | 9/1991 | Matsuda et al. | 536/28.2 |
| 5,223,608 | 6/1993 | Chou et al. | 536/28.5 |

FOREIGN PATENT DOCUMENTS

| | | |
|---|---|---|
| 0577304 | 1/1994 | European Pat. Off. . |
| 0587364 | 3/1994 | European Pat. Off. . |
| 51-026884 | 3/1976 | Japan . |
| 06192285 | 12/1992 | Japan . |
| 9312128 | 6/1993 | WIPO . |

OTHER PUBLICATIONS

Kochetkov et al., *Organic Chemistry of Nucleic Acids, Part B*, Plenum Press, New York, NY, 1972, pp. 465–466, see citation 166.

Goodman, "Chemical Syntheses and Transformations of Nucleosides," Ch. 2 in *Basic Principles in Nucleic Acid Chemistry*, Academic Press, New York, NY, 1974, pp. 142–143 (see citations 206–206e) pp. 177–190 (see relevant citations).

Rosenthal et al., "Nucleosides of Branched–Chain Nitromethyl, Cyanomethyl, and Aminomethyl Sugars," *Tetrahedron Letters*, (48), 4233–4235 (1970).

Cook & Moffatt, "Carbodiimide–Sulfoxide Reactions. VI. Syntheses of 2'–and 3'–Ketouridines," *J. Am. Chem. Soc.*, 89(11), 2697–2705 (1967).

Brodbeck & Moffatt, "Carbodiimide–Sulfoxide Reactions. IX. Synthesis of 2'–and 3'–Keto Derivatives of Cytidine," *J. Organic Chemistry*, 35(10), 3552–3558 (1970).

Tarkoy et al., "Nucleic–Acid Analogues with Constraint Conformation Flexibility in the Sugar–Phosphate Backbone ('Bicyclo–DNA')," *Helvetica Chimica Acta*, 76, 481–510 (1993).

Robins et al.(I), "Periodinane Oxidation, Selective Primary Deprotection, and Remarkably Stereoselective Reduction of tert–Butyldimethylsilyl–Protected Ribonucleosides. Synthesis of 9–(β–D–Xylofuranosyl)adenine or 3'–Deuterioadenosine from Adenosine," *J. Organic Chemistry*, 55(2), 410–412 (1990).

Chládek et al., "Aminoacyl Derivatives of Nucleosides, Nucleotides, and Polynucleotides. XVIII. Synthesis of 2'(3')–O–Aminoacyl Derivatives of Dinucleoside Phosphates," *J. Organic Chemistry*, 39(15), 2187–2193 (1974).

Kondo et al.(I), "Studies on Biologically Active Nucleosides and Nucleotides. 7. Synthesis of some $N^4$–Acylaminomethyl 2,2'–Anhydronucleosides," *J. Organic Chemistry*, 45(9), 1577–1581 (1980).

Kanai et al., "Pyrimidine Nucleosides. III. Reaction of Cytidine or $N^4$–Acetylcytidine with Partially Hydrolyzed Phosphorus Oxychloride," *Chem. Pharm. Bull.*, 18(12), 2569–2571 (1970).

Furukawa et al., "A Direct Synthesis of 3', 5'–Di–O–Acetyl–)2,2'–cyclouridine," *Chem. Pharm. Bull.*, 16(11), 2286–2288 (1968).

Kondo et al.(II), "Studies on Biologically Active Nucleosides and Nucleotides. @. A Convneint One–Step Synthesis of 2,2'–Anhydro–1–(3', 5'–di–O–acyl–β–D–arabinofuransyl)pyrimidines From Pyrimidine Ribonucleosides," *J. Organic Chemistry*, 42(17), 2809–2812 (1977).

(List continued on next page.)

*Primary Examiner*—John Kight
*Assistant Examiner*—L. Eric Crane
*Attorney, Agent, or Firm*—Brian P. Barrett; David E. Boone

[57] ABSTRACT

A process for the preparation of compounds of the formula:

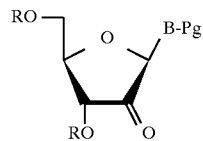

wherein Pg and R are protecting groups and B is a nucleobase. The process uses protected nucleobases to form 2,2'-anhydro nucleosides having the formula

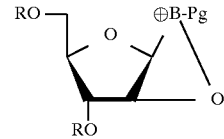

which are hydrolyzed to 2'-hydroxy intermediates which are then oxidized to the desired 2'-keto compounds. The compounds and intermediates are useful as antiviral and antitumor agents and as intermediates to 2,2'-anhydro-1-(β-D-arabinofuranosyl)cytosine (anhydro-ara-C) and 1-β-D-arabinofuranosylcytosine (Ara-C).

8 Claims, No Drawings

OTHER PUBLICATIONS

Brodbeck et al., "Carbodiimide–Sulfoxide Reactions. IX. Synthesis of 2'–and 3'–Keto Derivatives of Cytidine," *J. Organic Chemistry*, 35(10), 3552–3558 (1970).

Marcuccio et al., "Modified Nucleosides. II. Economical Synthesis of 2',3'–Dideoxycytidine," *Nucleosides & Nucleotides*, 11(10), 1695–1701 (1992).

Chwang et al. (III), "2'–O–Nitro–1–β–D–arabinofuranosylcytosine. A New Derivative of 1–β–D–arabinofuranosylcytosine That Resists Enzymatic Deamination and Has Antileukemic Activity," *J. Medicinal Chemistry*, 26(2), 280–288 (1983).

Samano et al., "Mild Periodinane Oxidation of Protected Nucleosides To Give 2'–and 3'–Ketonucleosides. The First Isolation of a Purine 2'–Deoxy–3'–ketonucleoside Derivative," *J. Organic Chemistry*, 55(18), 5186–5188 (1990).

Hansske et al.(I), "Nucleic Acid Related Compounds. 43. A Convenient Procedure for the Synthesis of 2' and 3'–Ketonucleosides," *Tetrahedron Letters*, 24(15), 1589–1592 (1983).

Hansske et al.(II), "2' and 3'–Ketonucleosides and Their *Arabino* and *Xylo* Reduction Products," *Tetrahedron*, 40(1), 125–135 (1994).

Robins et al. (II), "Nuclei Acid Rlated COmpounds. 74. Synthesis and Biological Activity of 2'(and 3')–Deoxy–2'(and 3')–methylenenucleoside Analogues That Function as Mechanism–Based Inhibitors of S–Adenosyl–L–homocysteine Hydrolase and/or Ribonucleotide Reductase," *J. Medicinal Chemistry*, 35(12), 2283–2293 (1992).

Ishida et al., "N$^4$–Acylnucleosides," *Chem. Abstracts*, 85, pp. 678–679, Abstr. N O. 124309g (1976); English language abstract of Japanese patent reference O supra attached to a complete copy of the patent in japanese.

Sakata et al., "Preparation of 1–(β–D–Erythropentofuran–u-losyl)pyrimidines as Interemdiates for Antitumor . . . [Agents]," *Chem. Abstracts*, 122, p. 1107, Abstract No. 188035e (1995); English language abstract of Japanese patent reference P supra attached to a complete copy of the patent in Japanese.

PROCESS FOR THE PREPARATION OF 2,2'-ANHYDRO- AND 2'-KETO-1-(3',5'-DI-O-PROTECTED-β-D-ARABINOFURANOSYL) NUCLEOSIDES

This application is a continuation of application Ser. No. 08/409,568, filed on March 24, 1995, now abandoned.

BACKGROUND OF THE INVENTION

The present invention relates to a process for the preparation of an intermediate compound of the formula:

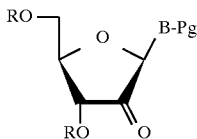

also known as a 2'-keto-1-(3',5'-di-O-protected-β-D-arabinofuranosyl)nucleoside, where R is a hydroxy-protecting group, Pg is a protecting group, and (B) is a nucleobase. Further, the present invention relates to an intermediate compound of the formula:

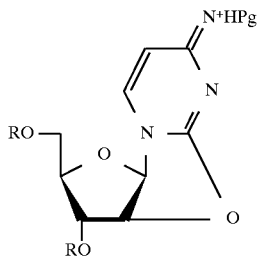

also known as 2,2'-anhydro-1-(3',5'-di-O-protected-β-D-arabinofuranosyl)-$N^4$-protected-pyrimidine. In particular the present invention relates to a process for the preparation of 1-(2'-keto-3',5'-di-O-acetyl-β-D-arabinofuranosyl)-$N^4$-acetylcytosine (I) and 2,2'-anhydro-1-(3',5'-di-O-acetyl-β-D-arabinofuranosyl)-$N^4$-acetylcytosine (IV). The compounds are useful as antiviral and antitumor agents and are intermediates to 1-(β-D-arabinofuranosyl)cytosine (Ara-C). In particular, the process includes steps of providing an amino-protecting group (Pg) for N of the nucleobase (B) and forming a boron tetrafluoride salt at the N-position; blocking the 3'- and 5'-hydroxy positions of the arabinofuranosyl group with an acyl group (R) and at the same time forming the 2,2'-anhydro group; hydrolyzing the 2,2'-anhydro group to a 2'-hydroxide group and then oxidizing the 2'-hydroxy group to a 2'-keto group. In this manner, the reaction to the 2'-keto group proceeds easily and in good yield.

The preparation of a 2,2'-anhydro-1-(β-D-arabinofuranosyl)cytosine-$N^4$-hydrotetrafluoroborate is generally described by Kondo, et al., *J. Org. Chem.*, 42(17), 2809–2812 (1977). In this process, boron trifluoride etherate, acetic anhydride and cytidine are reacted together with heating. N-acetyl protection of the $N^4$-position of the cytosine is not described. Kondo, et al., *J. Org. Chem.*, 45, 1577–1581 (1980) describe the preparation of an $N^4$ acetyl derivative of the compound of Kondo, et al., (1977) using acetic anhydride triethylamine with the compound (1a or 1b) of Kondo et al. (1977). The reactions are performed in two steps.

The protection of the $N^4$ position of cytidine is described in Marcuccico, et al., *Nucleosides and Nucleotides*, 11(10), 1695–1701 (1992). Acetic anhydride or an acetyl halide is reacted with cytidine. There was no suggestion of coupling this reaction with a reaction such as that of Kondo, et al. (1980). Chwang, et al., *J. Med. Chem.*, 26, 280–283 (1983) describe the preparation of a triacetyl cytosine (4) from a 2,2'-anhydrocytidine (2). Brodbeck, et al., *J. Org. Chem.*, 35(10), 3552–3558 (1970) describe the preparation of a $N^4$-protected cytidine.

Kondo, et al., *J. Org. Chem.*, 45, 1577–1581 (1980) also describe the hydrolysis of 2,2'-anhydro group to a 2'-hydroxy group.

Samano, et al., *J. Org. Chem.*, 55, 5186–5188 (1990) describe the use of the Dess-Martin reagent to form a 2'-keto nucleoside with protecting groups for the 3'- and 5'-hydroxy groups (O-triethyl or O-tosyl). The problem not solved by this reference is the need to protect the $N^4$ amino group of cytidine. Hansske, et al., *Tet. Letters*, 24(15), 1589–1592 (1983) describe a different process for forming a keto group from hydroxy compounds in nucleosides with a protected O-position (O-trityl). Hansske, et al., *Tetrahedron*, 40(1), 125–135 (1984) describe still another process for forming keto groups from hydroxy groups in O-protected ribonucleosides. Cook, et al., *J. Am. Chem. Soc.*, 89, 2697–2705 (1967) also describe an oxidation reaction to form a keto group without any discussion of a 2,2'-anhydro group. Enzymatic reactions to form 2'-keto groups are known as described in Robins, et al., *J. Med. Chem.*, 35, 2283–2293 (1992).

More recently, Japanese Patent application JP 06192285 described the oxidation of 1-β-D-arabinofuranosylpyrimidine nucleosides to the corresponding 2'-keto intermediates using chromic acid—see Derwent Abstract 94-260509/32.

It is therefore an object of the present invention to provide a novel process for the preparation of 2,2'-anhydro- and 2'-keto-1-(3',5'-di(-O-R)-β-D-arabinofuranosyl)-N-Pg-nucleosides in good yield. These and other objects will become increasingly apparent by reference to the following description.

DETAILED DESCRIPTION AND PREFERRED EMBODIMENTS

The following definitions refer to the various terms used throughout this disclosure. The term "halo" refers to fluoro, chloro, bromo, and iodo. The term "alkyl" refers to the straight and branched aliphatic radicals of 1 to 8 carbon atoms such as methyl, ethyl, propyl, isopropyl, n-butyl, sec-butyl, tert-butyl, n-pentyl, 2,2-dimethylpropyl, hexyl, octyl, and the like. The term "substituted alkyl" refers to alkyl which is substituted by one or more groups selected from hydroxy, halo, and (alkyl)-O-, such as trifluoromethyl, 2-methoxyethyl, 3-hydroxy-6-methylheptyl, and the like.

The present invention relates to a process for the preparation of a 2'-ketonucleoside of the formula

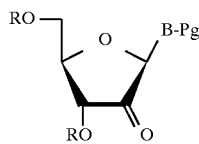

wherein -B- is a nucleobase as defined below attached to the tetrahydrofuran ring through the nitrogen atom of the nucleobase ring, -Pg is a protecting group, and each R is a hydroxy-protecting group, which comprises:

(a) reacting a first intermediate 2'-hydroxy-nucleoside of the formula

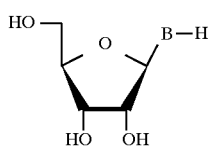

with a protecting group forming compound in a solvent to form a second protected intermediate of the formula

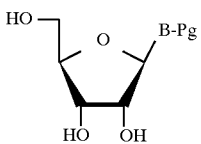

(b) reacting the second protected intermediate with boron trifluoride and a reaction compound selected from the group consisting of an anhydride and a carbonyl halide to form a third cyclic oxide intermediate of the formula

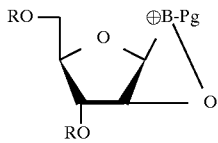

wherein the oxide is between the alpha position of the nucleobase and the 2'-position of the cytosine and replaces the alpha keto group;

(c) reacting the third cyclic oxide intermediate with a base in water to form a fourth 2'-hydroxy intermediate of the formula

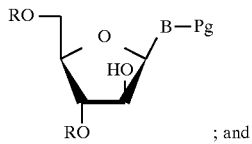

(d) oxidizing the fourth 2'-hydroxy intermediate to produce the 2'-ketonucleoside.

B is a nucleobase selected from the group consisting of

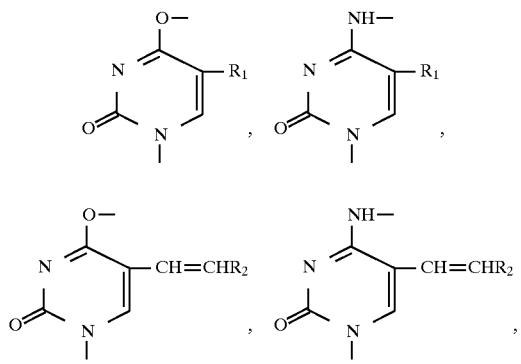

-continued

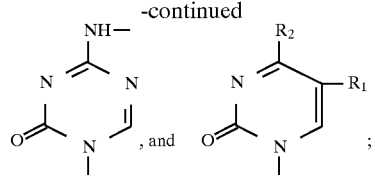

wherein $R_1$ is selected from the group consisting of hydrogen, alkyl, substituted alkyl and halo; $R_2$ is selected from the group consisting of hydrogen, alkyl and halo. In the case of the latter nucleobase as defined above for B, there will be no need to protect the nucleobase with a protecting group Pg and the resulting 2'-ketonucleoside will not bear a Pg group.

It will be noted that in the depiction of the cyclic oxide intermediate above there is an additional point of attachment to the nucleobase—this third bond is through the carbon atom adjacent to the nitrogen atom that is bonded to the tetrahydrofuran ring; this carbon atom is the same as that which bears the carbonyl group as drawn above. An example of this structure is described further below as compound IV.

In a preferred embodiment of the present process the nucleobase derivative is of the formula

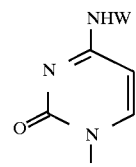

wherein W is acetyl. Other monocyclic groups with a 2-keto group (B) which can be used are, for instance, uracil, thymidine, and 5-iodouracil.

The protecting groups designated Pg in formulae throughout this specification denotes a group which is intentionally introduced during a portion of the synthetic process to protect the amino or hydroxy group which may otherwise react in the course of chemical manipulations, and is then removed at a later stage of the synthesis. Numerous reactions for the formation and removal of such a protecting group are described in a number of standard works including, for example, "Protective Groups in Organic Chemistry", Plenum Press, (London and New York, 1973); Greene, Th. W., "Protecting Groups in Organic Synthesis", Wiley, (New York, 1981); and "The Peptides", Vol. I, Schrooder and Lubke, Academic Press, (London and New York, 1965). Typically, an acyl group which is selectively removable under mild conditions, such as for example, a formyl group, a lower alkanoyl group of from 2 to 8 carbon atoms which is substituted at the 1-position, such as trifluoroacetyl, an optionally substituted benzoyl group, etc., is employed. Preferably the protecting group (Pg) is an acetyl group. A benzoyl group is also commonly used.

The intermediates employed in this invention are of a nature such that the 3'- and 5'-hydroxy groups must be protected to keep them from reacting with the nucleobase, or being decomposed in some manner. The hydroxy-protecting groups R are derived from the anhydride or carbonyl halide reagent used in converting the amino protected nucleoside intermediate to the cyclic oxide intermediate. Chemists are accustomed to choosing groups which can be efficiently placed on hydroxy groups, and which can be easily removed when the reaction is complete. The R-group is an acyl group which is selectively removable under mild conditions, such as for example, a formyl group, or a lower alkanoyl group of from 2 to 8 carbon atoms which is optionally substituted at the 1-position, such as trifluoroacetyl. Suitable such acyl groups are described in standard textbooks, such as Chapter 3, of Protective Groups in Organic Chemistry, McOmie, Ed., Plenum Press, N.Y. (1972); and Chapter 2 of Protective Groups in Organic Synthesis, Greene, John Wiley & Sons, N.Y. (1981). For example, hydroxy-protecting groups include such as formyl, acetyl, 2-chloroacetyl, propionyl, benzoyl, triphenylacetyl, trifluoroacetyl, phenoxycarbonyl, methoxyacetyl, phenoxyacetyl, isobutyryl, ethoxycarbonyl, benzyloxycarbonyl, and the like; such groups are introduced when the corresponding acid anhydride or acid halide are employed. As noted above, acetyl is the preferred R-group and acetic anhydride is the preferred reagent for converting the second protected nucleoside intermediate to the cyclic oxide intermediate.

The nucleobase (B) is protected in step (a) before any further reaction. Preferably an acetyl group is introduced using acetic anhydride in a solvent such as methanol. The reaction temperature is between about 50° and 100° C. (up to the reflux temperature of the mixture).

The 2,2'-anhydro group is formed in step (b) using boron trifluoride and a compound selected from the group consisting of an anhydride and a carbonyl halide, preferably in acetonitrile as a non-reactive solvent. At the same time, the 3'- and 5'-positions of the arabinofuranosyl group are protected, usually with an O-acetyl group. The reaction temperature is between about 50° and 100° C. (up to the reflux temperature of the mixture).

The 2,2'-anhydro group is converted to a hydroxide group by an aqueous hydrolysis reaction with a base in step (c). The base is preferably an inorganic base such as sodium bicarbonate. The reaction temperature is preferably between about 0° and 5° C.

In step (d), the 2-hydroxy group is oxidized using a conventional reaction. Preferably acetic anhydride in dimethylsulfoxide or Dess-Martin reagent (1,1,1-tris(acetyloxy)-1,1-dihydro-1,2-benziodoxol-3(1H)-one) is used. The Dess-Martin reaction is conducted at between about 0° and 30° C. The acetic anhydride reaction is preferably conducted at between about 0° and 30° C.

The present invention also relates to an intermediate (IV) of the formula:

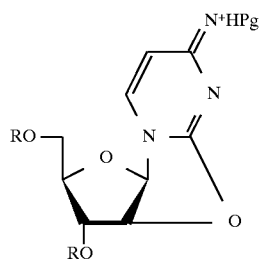

wherein R and Pg are as previously defined. Most preferably R and Pg are acetyl group.

The preferred synthetic route of the present invention is:

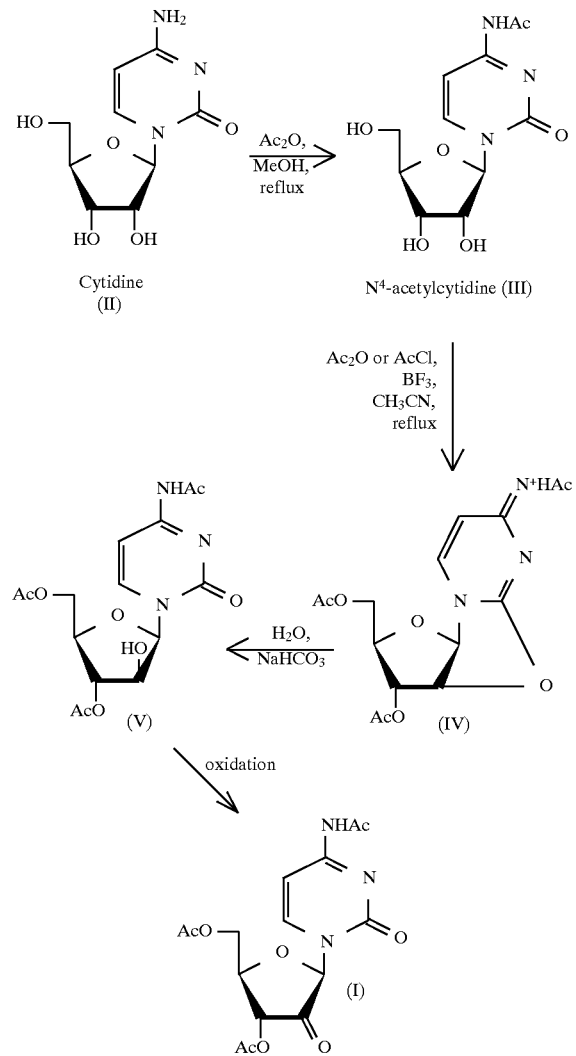

where Ac is acetyl. It has been found that the acylation of the $N^4$ of the cytosine group in step (a) prior to formation of the 2,2'-anhydro ring group between the 2'-hydroxy and the 2'-keto cytosine gives much better yields than $N^4$-acylation after the formation of the 2,2'-anhydro ring group. By acetylating first, a three step yield of $N^4,O^{3'},O^{5'}$-triacetyl-1-β-D-arabinofuranosylcytosine (I) from cytidine of 49% was achieved. This more than doubles the yield obtained by acetylating subsequent to ring closure (22% overall) (Kondo 1980). The oxidation of the 2'-hydroxyarabino derivative (V) in step (d) is in the unnatural configuration, and provides the 2'-keto derivative (I).

EXAMPLE 1

Step 1

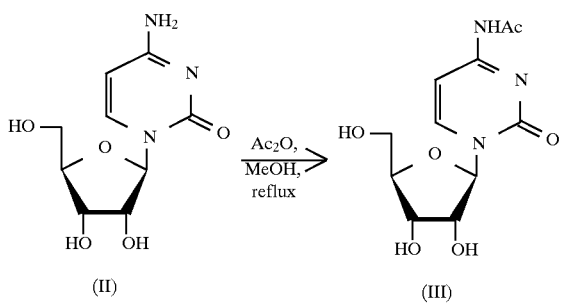

The procedure of Marcuccio, et al., *Nucleosides and Nucleotides*, 11, 1695–1701 (1992) was used.

Cytidine (3.000 g, 12.33 mmol) was placed in a dry, nitrogen flushed flask equipped with mechanical stirrer and condenser. It was dissolved in methanol (40 mL) and heated to reflux. Acetic anhydride (11.6 mL, 12.6 g, 124 mmol) was added via an addition funnel over 2 hours. The reaction mixture was refluxed for an additional 1 hour. The reaction mixture was then cooled to 0° C. and filtered, affording the acetyl protected product as a colorless crystalline solid (3.114 g, 89%): IR (neat) 3473, 3265, 1718, 1643, 1491 cm$^{-1}$; $^1$H NMR (DMSO) δ 10.89 (s, 1H), 8.43 (d, 1H, J=7.5 Hz), 7.19 (d, 1H, J=7.5 Hz), 5.78 (d, 1H, J=2.6 Hz), 5.49 (d, 1H, J=4.7 Hz), 5.17 (t, 1H, J=5.0 Hz), 5.06 (d, 1H, J=4.7 Hz), 3.99 (s, 2H), 3.90 (s, 1H), 3.65 (m, 2H), 2.10 (s, 3H); $^{13}$C NMR (DMSO) δ 171.1, 162.3, 154.7, 145.4, 95.2, 90.2, 84.2, 74.5, 68.7, 59.9, 24.4.

Analysis for $C_{11}H_{15}N_3O_6$:
Calc.: C, 46.32; H, 5.30; N, 14.73;
Found: C, 46.02; H, 5.48; N, 14.56.

Step 2

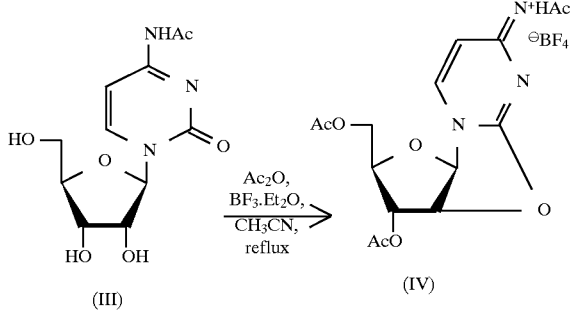

N$^4$-acetylcytidine (III) was placed in a dried, nitrogen flushed flask equipped with condenser, mechanical stirrer, and addition funnel. The substrate was dissolved in acetonitrile (75 mL). Boron trifluoride etherate (3.8 mL, 4.3 g, 31 mmol) was then added. The reaction mixture was heated to reflux and acetic anhydride was added dropwise via an addition funnel. After 1 hour the reaction mixture was concentrated to an oil and triturated with diethyl ether (75 mL)/isopropyl alcohol (50 mL) to afford the product as a white powder (3.055 g, 68%): IR (neat) 1747, 1652, 1569, 1469, 1228 cm$^{-1}$; $^1$H NMR (DMSO) δ 11.73 (s, 1H), 9.00 (d, 1H, J=7.3 Hz), 8.14 (d, 1H, J=7.3 Hz), 6.86 (d, 1H, J=6.2 Hz), 5.91 (d, 1H, J=6.2 Hz), 5.48 (d, 1H, J=2.4 Hz), 4.75 (m, 1H), 4.19 (dd, 1H, J=12.6, 5.1 Hz), 3.96 (dd, 1H, J=12.6, 2.9 Hz), 2.25 (s, 3H), 2.12 (s, 3H), 1.82 (s, 3H); $^{13}$C NMR δ 172.7, 171.0, 170.9, 166.4, 160.6, 148.3, 106.1, 93.4, 89.8, 85.1, 77.6, 64.6, 26.0, 21.8, 21.3; MS (FAB) m/z 352, 309, 155, 152, 135, 119.

Analysis for $C_{15}H_{18}N_3O_7F_4B$:
Calc.: C, 41.03; H, 4.13; N, 9.57;
Found: C, 40.65; H, 4.18; N, 9.58.

EXAMPLE 2

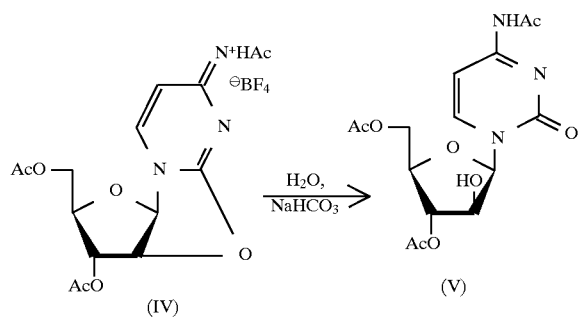

The triacetylanhydro-substrate IV (0.695 g, 1.97 mmol) was placed in a dried, nitrogen flushed flask and dissolved in an aqueous sodium bicarbonate (0.239 g, 2.9 mmol in 14 mL) solution. The reaction was allowed to proceed for 17 hours after which it was filtered to afford the product as a white powder (0.586 g, 81%): IR (neat) 3306, 1722, 1658, 1613, 1493, 1249 cm$^{-1}$; $^1$H NMR (CDCl$_3$) δ 10.87 (s, 1H), 7.96 (d, 1H, J=7.5 Hz), 7.21 (d, 1H, J=7.5 Hz), 6.05 (m, 2H), 4.93 (d, 1H, J=1.5 Hz), 4.38 (dd, 1H, J=11.3, 7.3 Hz), 4.22 (m, 3H), 2.09 (s, 6H), 2.04 (s, 3H); $^{13}$C NMR (CDCl$_3$) δ 172.1, 171.4, 170.8, 163.5, 155.5, 147.7, 95.7, 88.4, 81.5, 79.6, 72.7, 64.3, 25.5, 21.8, 21.7; MS (FAB) m/z 370 (M+), 309, 155, 135, 119.

Analysis for $C_{15}H_{19}N_3O_8$:
Calc.: C, 48.78; H, 5.18; N, 11.38;
Found: C, 45.04; H, 4.99; N, 10.73.

EXAMPLE 3

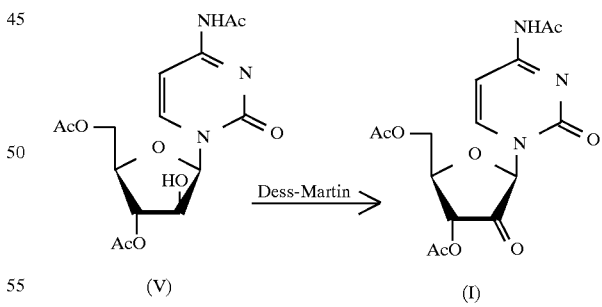

The 2'-hydroxy-triacetyl substrate (V) (0.325 g, 0.88 mmol) was placed in a dried nitrogen flushed flask and dissolved in acetonitrile (5 mL). Dess-Martin reagent (0.560 g, 1.32 mmol) was then added to the rapidly stirred mixture. The reaction was allowed to proceed for 72 hours after which it was concentrated in vacuo and subjected to flash column chromatography (5% isopropyl alcohol in ethyl acetate) affording the product as a colorless crystalline solid (0.205 g, 63%): IR (neat) 1742, 1670, 1479, 1325, 1053 cm$^{-1}$; $^1$H NMR (CD$_2$Cl$_2$) δ 9.84 (s, 1H), 7.71 (d, 1H, J=7.5

Hz), 7.48 (d, 1H, J=7.5 Hz), 5.41 (s, 1H), 5.12 (d, 1H, J=6 Hz), 4.46 (2H, m), 4.34 (1H, m), 2.21 (3H, s) 2.14 (3H, s), 2.04 (3H, s); $^{13}$C NMR δ 200.4, 171.1, 170.9, 170.8, 164.9, 155.1, 149.2, 97.9, 87.5, 79.2, 72.4, 64.7, 25.1, 20.8, 20.4.

Analysis for $C_{15}H_{17}N_3O_8 \cdot H_2O$:
Calc.: C, 46.88; H, 4.97; N, 10.90;
Found: C, 46.66; H, 4.77; N, 10.18.

The use of Dess-Martin reagent is preferred.

EXAMPLE 4

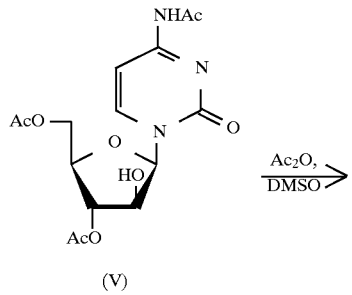

(V)

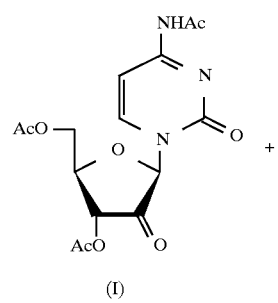

(I)

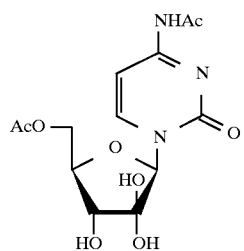

To a 25 mL round bottomed flask was added dimethyl sulfoxide (DMSO) (6 mL); and acetic anhydride (6 mL, ~6 mmol). The reaction mixture was stirred for 30 minutes. The compound (V) of Example 2 was added to the reaction mixture (0.50 g, 1.4 mmol).

The reaction mixture was stirred overnight. Water (10 mL) and ethyl acetate (EtOAc) (10 mL) were added for an extraction. The organic and aqueous layers were separated. The organic layer was washed with water (2×10 mL). The organic layer was dried over anhydrous magnesium sulfate. The ethyl acetate was stripped from the organic layer to produce an oil. The product (I) was purified by twice adding toluene (10 mL) and distilling the toluene to produce a white solid.

$^1$H-NMR (CD$_2$Cl$_2$) showed a mixture of two compounds which were the product (I) and a 2'-ketohydrate in a weight ratio between about 60:40. The product (I) can be purified by chromatography.

It is intended that the foregoing description be only illustrative of the present invention and that the present invention be limited only by the hereinafter appended claims.

I claim:

1. A process for the preparation of a 2'-keto-nucleoside intermediate of the formula

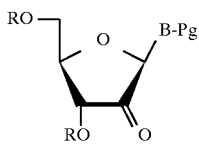

wherein -B- is a nucleobase attached to the tetrahydrofuran ring through the nitrogen atom of the nucleobase ring which is selected from the group consisting of

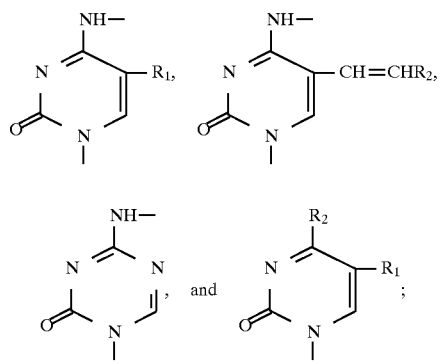

wherein $R_1$ is selected from the group consisting of hydrogen, alkyl, substituted alkyl and halo; $R_2$ is selected from the group consisting of hydrogen, alkyl and halo, -Pg is a protecting group which is acetyl, trifluoroacetyl or an optionally substituted benzoyl group, and each R is a hydroxy-protecting group which is acetyl or trifluoroacetyl, which comprises:

(a) reacting a first intermediate 2'-hydroxy-nucleoside of the formula

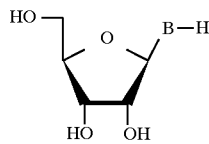

with a protecting group forming compound in a solvent to form a second protected intermediate of the formula

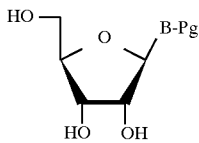

(b) reacting the second protected intermediate with boron trifluoride and a reaction compound selected from the group consisting of an anhydride and a carbonyl halide to form a third cyclic oxide intermediate of the formula

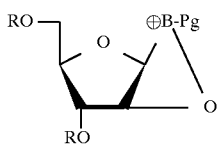

wherein the oxide is between the alpha position of the nucleobase and the 2'-position of the cytosine and replaces the alpha keto group;

(c) reacting the third cyclic oxide intermediate with a base in water to form a fourth 2'-hydroxy intermediate of the formula

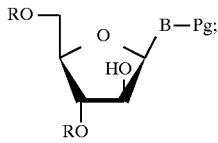

and (d) oxidizing the fourth 2'-hydroxy intermediate to produce the 2'-ketonucleoside.

2. A process for the preparation of a 2'-ketocytidine nucleoside first intermediate of the formula

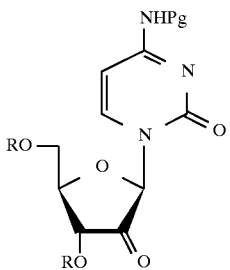

wherein Pg is a protecting group which is acetyl, trifluoroacetyl or an optionally substituted benzoyl group and R is a hydroxy-protecting group which is acetyl or trifluoroacetyl which comprises:

(a) reacting cytidine with an amine protecting group forming compound in a solvent to form a third intermediate of the formula

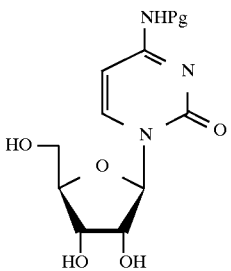

(b) reacting the third intermediate with boron trifluoride and a reactant compound selected from the group consisting of an anhydride and carbonyl halide to form a fourth intermediate of the formula

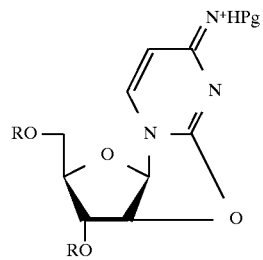

wherein R is a hydroxy-protecting group;

(c) reacting the fourth intermediate with a base in water to form a fifth intermediate of the formula

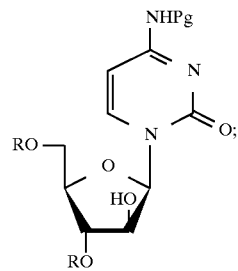

and (d) oxidizing the fifth intermediate to produce the 2'-ketocytidine nucleoside.

3. The process of claim 2 wherein the amine protecting group forming compound in step (a) is acetic anhydride and Pg is an acetyl group.

4. The process of claim 2 wherein the anhydride in step (b) is acetic anhydride and R is an acetyl group.

5. The process of claim 2 wherein the base is sodium bicarbonate.

6. The process of claim 2 wherein the oxidation is with acetic anhydride in dimethylsulfoxide.

7. The process of claim 2 wherein the oxidation is with 1,1,1-tris(acetyloxy)-1,1-dihydro-1,2-benziodoxol-3(1H)-one, also known as Dess-Martin reagent.

8. The process of claim 2 wherein the amine protecting group forming compound in step (a) is acetic anhydride and wherein the protecting group is an acetyl group and Pg is an acetyl group, wherein the anhydride in step (b) is acetic anhydride and R is an acetyl group; wherein the base is sodium bicarbonate; and wherein the oxidation is with 1,1,1-tris(acetyloxy)-1,1-dihydro-1,2-benziodoxol-3(1H)-one also known as Dess-Martin reagent.

* * * * *